(12) United States Patent
Zeng

(10) Patent No.: US 9,297,817 B2
(45) Date of Patent: Mar. 29, 2016

(54) METHODS AND SYSTEMS FOR AUTOMATED PIPETTE TRACKING

(75) Inventor: Lei Zeng, Irvine, CA (US)

(73) Assignee: Actrace, LLC, Irvine, CA (US)

( * ) Notice: Subject to any disclaimer, the term of this patent is extended or adjusted under 35 U.S.C. 154(b) by 339 days.

(21) Appl. No.: 14/113,839

(22) PCT Filed: Apr. 23, 2012

(86) PCT No.: PCT/US2012/034656
§ 371 (c)(1),
(2), (4) Date: Nov. 21, 2013

(87) PCT Pub. No.: WO2012/158308
PCT Pub. Date: Nov. 22, 2012

(65) Prior Publication Data
US 2014/0130614 A1    May 15, 2014

Related U.S. Application Data

(60) Provisional application No. 61/485,717, filed on May 13, 2011.

(51) Int. Cl.
| | | |
|---|---|---|
| *G01N 35/00* | (2006.01) | |
| *B01L 3/02* | (2006.01) | |
| *B01L 3/00* | (2006.01) | |
| *G01N 35/10* | (2006.01) | |

(52) U.S. Cl.
CPC ........ *G01N 35/00584* (2013.01); *B01L 3/0237* (2013.01); *B01L 3/527* (2013.01); *G01N 35/1011* (2013.01); *B01L 2200/025* (2013.01); *B01L 2200/143* (2013.01); *B01L 2200/148* (2013.01); *B01L 2300/027* (2013.01); *B01L 2300/0654* (2013.01); *B01L 2300/0829* (2013.01)

(58) Field of Classification Search
None
See application file for complete search history.

(56) References Cited

U.S. PATENT DOCUMENTS

| | | | |
|---|---|---|---|
| 4,692,609 A | 9/1987 | Pettersson | |
| 4,830,832 A | 5/1989 | Arpagaus et al. | |
| 5,443,791 A * | 8/1995 | Cathcart | G01N 35/0098 422/561 |
| 5,906,795 A | 5/1999 | Nakashima et al. | |
| 6,601,433 B2 | 8/2003 | Kriz et al. | |
| 7,544,330 B2 | 6/2009 | Ryle | |
| 7,544,336 B2 | 6/2009 | Powell | |

(Continued)

FOREIGN PATENT DOCUMENTS

WO    2009130318 A2    10/2009

OTHER PUBLICATIONS

Sep. 24, 2014 Office Action Summary in Chinese Application 201280017562.6 entitled "Method and Systems for Automated Pipette Tracking," with English translation (4 pp.).

(Continued)

*Primary Examiner* — Herzon E Williams
*Assistant Examiner* — Mark A Shabman
(74) *Attorney, Agent, or Firm* — Silicon Edge Law Group LLP; Arthur J. Behiel

(57) ABSTRACT

Described are pipetting systems that automatically track the dispensing and extracting of reagents to and from arrays of well locations. The systems track the position of a pipette with respect to the well locations, and selectively illuminate those locations to indicate the progress of pipetting operations. Control logic can shepherd pipetting processes, indicating errors and guiding the user.

29 Claims, 2 Drawing Sheets

(56) References Cited

U.S. PATENT DOCUMENTS

| | | | |
|---|---|---|---|
| 7,726,212 | B2 | 6/2010 | Magnussen et al. |
| 7,976,793 | B2 | 7/2011 | Solotareff et al. |
| 2002/0021222 | A1 | 2/2002 | Howitz et al. |
| 2006/0188406 | A1 | 8/2006 | Frost |
| 2007/0286770 | A1 | 12/2007 | Magnant et al. |
| 2008/0031774 | A1 | 2/2008 | Magnant et al. |
| 2008/0042839 | A1 | 2/2008 | Grater et al. |
| 2009/0189878 | A1 | 7/2009 | Goertz et al. |
| 2011/0160909 | A1* | 6/2011 | Glauser ............ G01N 35/00722 700/264 |
| 2013/0330230 | A1* | 12/2013 | Uri ....................... G01N 21/658 422/69 |

OTHER PUBLICATIONS

Sep. 24, 2014 Office Action in Chinese Application 201280017562.6 entitled "Method and Systems for Automated Pipette Tracking" (3 pp.).

Oct. 15, 2014 Attorney Summary of Sep. 24, 2014 Office Action in Chinese Application 201280017562.6 entitled "Method and Systems for Automated Pipette Tracking" with English translation (3 pp.).

Jan. 9, 2015 Chinese-language response to Sep. 24, 2014 Office Action in Chinese Application 201280017562.6 entitled "Method and Systems for Automated Pipette Tracking" with English translation (3 pp.).

May 12, 2015 Office Action Summary in Chinese Application 201280017562.6 entitled "Method and Systems for Automated Pipette Tracking," with English translation (4 pp.).

May 12, 2015 Office Action in Chinese Application 201280017562.6 entitled "Method and Systems for Automated Pipette Tracking" (4 pp.).

May 27, 2015 Attorney Summary of May 12, 2015 Office Action in Chinese Application 201280017562.6 entitled "Method and Systems for Automated Pipette Tracking" (3 pp.).

Jul. 10, 2015 Response to May 12, 2015 Office Action in Chinese Application 201280017562.6 entitled "Method and Systems for Automated Pipette Tracking" (6 pp.).

Jul. 10, 2015 amended claims for response to May 12, 2015 Office Action in Chinese Application 201280017562.6 entitled ,"Method and Systems for Automated Pipette Tracking" (6 pp.).

Mark-up version of amended claims in Chinese Application 201280017562.6 entitled "Method and Systems for Automated Pipette Tracking" (6 pp.).

Gilson S.A.S., Trackman(tm), Guiding You to Success! (Brochure from Gilson, Inc., 6 pages, 2009).

BioTX, WellAware Systems Overview, online brochure from BioTX Automation, Inc., http://biotx.net/products/wellaware, 4 pages, downloaded Apr. 30, 2011.

Gilson S.A.S., Trackman(tm), Guiding You to Success! (online brochure from Gilson, Inc., 4 pages, downloaded Apr. 30, 2011).

Matrix Technologies Corporation, Handheld Pipetting Systems, Thermo Scientific Matrix Memowell, downloaded Apr. 30, 2011 (copyright 2009).

Gilson S.A.S., Trackman (tm), User's Guide (Gilson, Inc., 16 pages, Oct. 2009).

International Search Report, PCT/US2012/034656, mailed Nov. 28, 2012 (6 pages).

* cited by examiner

METHODS AND SYSTEMS FOR AUTOMATED PIPETTE TRACKING

FIELD

The present invention relates to method and systems for pipetting reagents for use in various kinds of analysis, such as immunoassays and DNA analysis.

BACKGROUND

Transferring reagents to, from, or between vials—a process commonly referred to as "pipetting"—is a basic function for most life science and chemical labs. Vials, also called "tubes" or "wells," can be small and are commonly arrayed in considerable numbers. Pipetting large numbers of samples is repetitive and prone to human error. Unfortunately, such errors can result in grave consequences, especially in clinical diagnostic and forensic labs.

A number of companies have commercialized semi-automated pipetting tracking devices to reduce pipetting errors. For example, some pipetting systems position arrays of wells over similar arrays of visible light-emitting diodes (LEDs) to selectively illuminate the wells from beneath. Other systems employ an LCD screen in lieu of an array of LEDs for the same purpose, as detailed in U.S. Patent Publication No. US 2006/0188406 to James Dahle Frost III. Users of such devices can use this lighting to keep track of which wells will be subjected to the next pipetting step. These systems require the user to select an illumination pattern specifying a pipetting order. The user then manually advances to a next well or set of wells after each pipetting step, or advances to the next well or set of wells responsive to a preset timer. The manual step can include pressing a button, a foot switch, or passing a sensor outside the pipetting zone. These manual steps add to the workload and are also subject to human error.

BRIEF DESCRIPTION OF THE DRAWINGS

The subject matter disclosed is illustrated by way of example, and not by way of limitation, in the figures of the accompanying drawings and in which like reference numerals refer to similar elements and in which.

DESCRIPTION

Figure 1A:
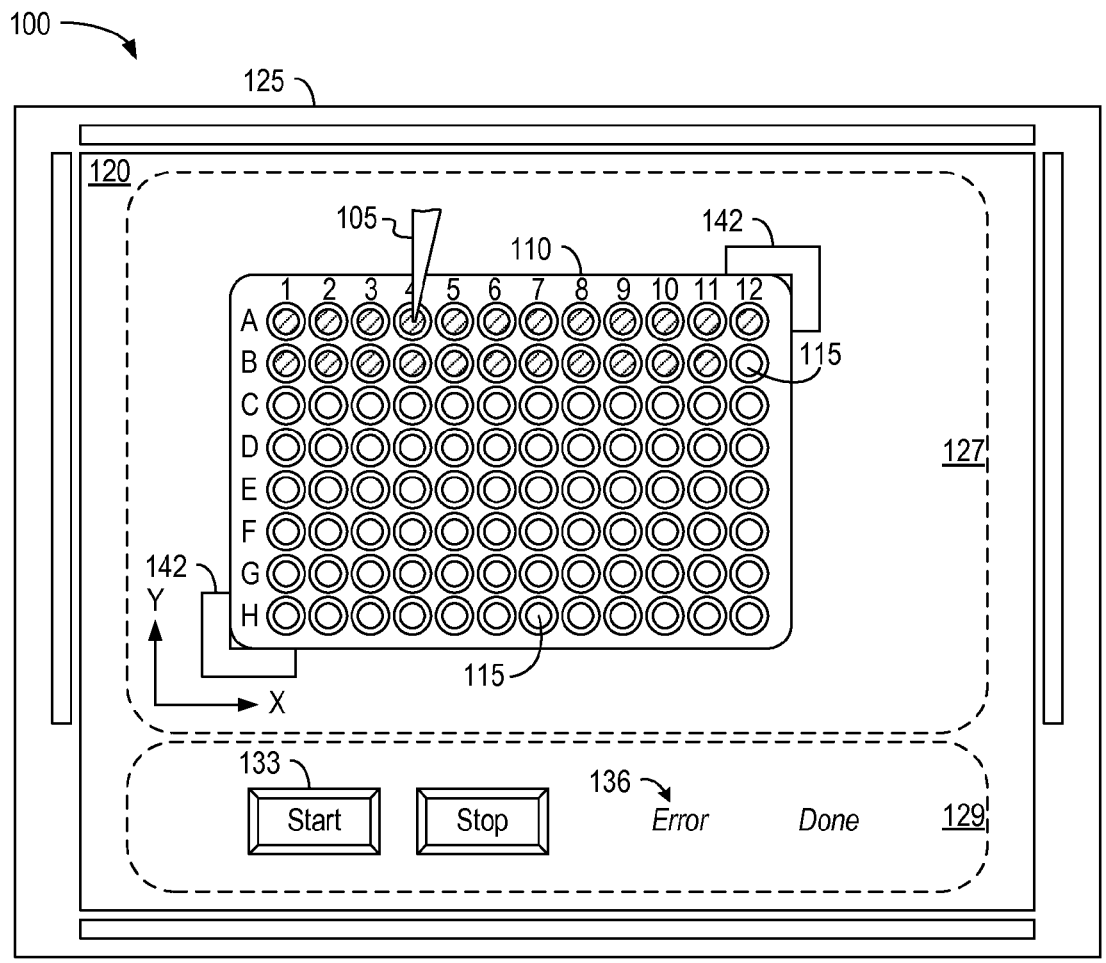
FIGS. 1A and 1B depict a system 100 for tracking the position of a pipette 105 with respect to a well plate 110.
Figure 1B:
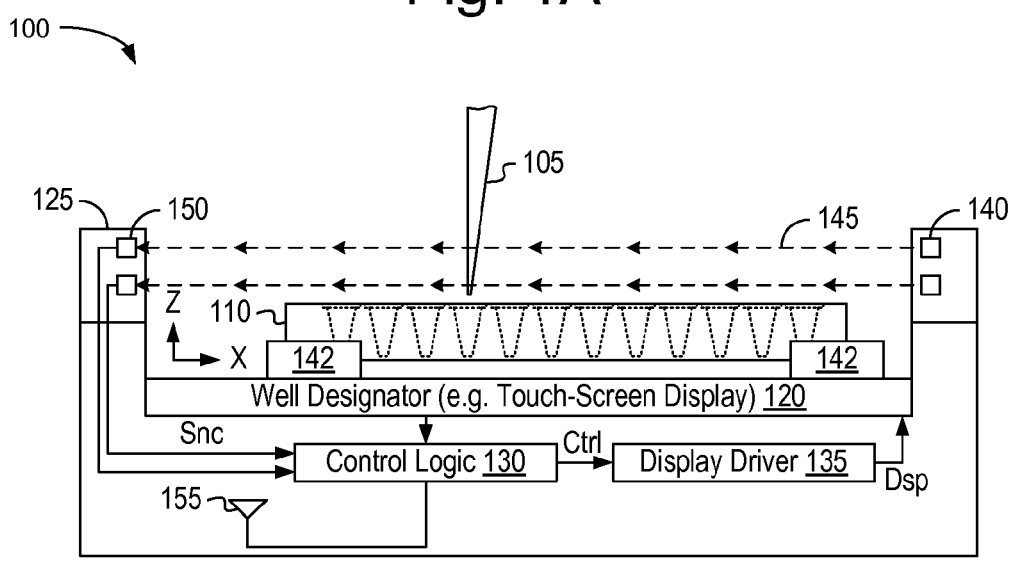

FIGS. 1A and 1B depict a system 100 for tracking the position of a pipette 105 with respect to a well plate 110 that includes an array of well locations 115 defining an X axis and a Y axis. System 100 includes a well designator 120 that selectively directs light to one or more well locations responsive to control signals Ctrl. Illuminated well locations 115 are highlighted using cross-hatching, which illumination indicates e.g. that the respective location was the subject of a prior pipetting operation.

A sensor 125 along the periphery of well plate 110 is positioned above well locations 115, from a perspective along a Z axis normal to the X and Y axes, to detect positions of pipette 105 with respect to the well locations. Well plate 110 is a microplate with integrated vials in this example, but other types of well plates (e.g., microplates or racks that support discrete vials) can also be used. Well designator 120 is a touchscreen display in this embodiment, and is divided into a well area 127 and a user-interface (UI) area 129. As detailed below, sensor 125 monitors pipette activity within area 127 and users of system 100 can enter commands via the touch-sensitive UI area 129.

Control logic 130, such as a central processing unit (CPU) or microcontroller, receives sensory signals Snc from sensor 125 and UI signals input from UI area 129. Control logic 130 derives control signals Ctrl from the sense and UI signals and feeds them to a display driver 135. Display driver 135, in turn, issues conventional display signals Dsp to control well designator 120.

Sensor 125, in this embodiment, includes arrays of infrared photodiodes 140 that produce beams of light 145 to photoreceptors 150. In one embodiment sensor 125 is a light-based touchscreen of the type detailed in U.S. Patent Publication No. US 2009/0189878 to Goertz et al. In such screens, light sources produce beams of light that can be broken to detect the presence of pipette 105 or e.g. a user's finger. Sensor 125 can determine the position of a pipette or finger relative to the X and Y axes, and consequently relative to well locations 115. Some embodiments may support different arrangements of sensors, such as to support parallel planes of light 145 (sensor planes), to provide a measure of pipette angle, for example. Incidence-angle sensitivity can be used to more precisely locate the tip of pipette relative to the well locations. Some embodiments may only determine the position of a pipette or finger relative to the Z axis, without determining the accurate position to the X and Y axes. The Z axis detection can be used to advance illumination to a next well or set of wells based on the preselected illumination pattern specifying a pipetting order.

Control logic 130 can be configured to ignore signals from sensor 125 that correspond to area 129, leaving that "user-interface" area for touch-based user input. Control logic 130 can also be configured to ignore signals from the touchscreen within well area 127. Sensor 125 omits unneeded lights and photoreceptors adjacent area 129 along the Y axis adjacent in this embodiment. Area 129 is shown to include "buttons" 133, which are virtualized implementations of e.g. keys of a keyboard or other types of graphical user interfaces. Area 129 can also provide user output, such as alarms 136 or other types of messages. UI area 129 can thus be used to calibrate and otherwise provide input for control logic 130.

System 100 additionally includes alignment mechanisms 142 that serve as indices for aligning well plate 127 relative to well designator 120, and that may double as well spacers to establish a desired spacing between light beams 145 and the tops of well locations 115. Closer spacing renders system 100 less susceptible to location errors due to pipette angle. The spacing of sensor 125 is adjustable along the Z axis in other embodiments to facilitate adjustment between beams 145 and the surface of well designator 120.

Display 120 can react to sensor 125, some other sensor (e.g., capacitive sensors in the display), or both, as noted previously. In still other embodiments control logic 130 is equipped with an antenna 155 or wired connection that allows control logic 130 to communicate with pipette 105. As discussed in more detail in connection with FIG. 2, antenna 155 allows control logic 130 to receive user input and other information a pipette signals from pipette 105 (e.g., dosage amounts, number of pipette channels, completion of a pipetting operation, and error messages), and can allow control logic 130 to communicate information to pipette 105. System 100 can also include e.g. a microphone and speaker to facilitate interaction between a user and control logic 130.

With reference to FIG. 1A, each cross-hatched well location 115 may be assumed to indicate a well that has been subjected to a pipetting operation, such as receiving a dose of a reagent, and that has consequently been illuminated (e.g., by green light). The next well location 115, at Cartesian coordinate A12, is not illuminated, or may be illuminated with a different color than the other well locations, to identify it as a "next" well location to receive a pipetting operation. The user would thus place the pipette in proximity to the next well location and e.g. provide the dose of reagent. System 100 would sense the proximity of pipette 105 to the well location 115 at location A12 and change the corresponding illumination to indicate receipt of the reagent. The illumination parameters can be modified to suit different needs. For example, some assays may be sensitive to certain lights. It will be desirable to illuminate wells that have not received the reagent, and turn off illumination on wells that have received the reagent. Users can also illuminate only the wells subject to next pipetting step to minimize the overall light exposure, or choose certain light colors that will not interfere with the assays.

The user may miss a well location, or may subject the same well location to multiple pipetting operations. In either case system 100 uses the sensed coordinate of pipette 105 to identify the error and provide appropriate user feedback. In embodiments in which pipette 105 is capable of transmitting indicia of a pipetting operation, such as a signal indicating depression of a plunger, control logic 130 can use this information along with the location information to identify a pipetting operation.

Well area 127 is the surface of a touchscreen in this embodiment, but may be e.g. a standard display or an array of lights (e.g. light-emitting diodes). In other embodiments well designator 120 can uniquely designate wells or collections of wells using by reference to row(s), column(s), or both. For example, the text "B12," or icons or lights adjacent row B and column 12, may designate the next well location 115 in FIG. 1A. Other means of uniquely designating well locations or collections of well locations will be evident to those of skill in the art.

In still other embodiments the well designator can transmit light to well plate 110 from above, as by projecting an image or light beams that selectively illuminate well locations 115. Such illumination preferably impinges well plate 110 at an angle with respect to the Z axis so the pipette does not overly interfere with the illumination. Well designator 120 may be calibrated with control logic 130 for different sizes, numbers, and spacing of well locations 115. Illumination patterns specifying a pipetting order can then be illuminated to guide the user. Other embodiments omit such calibration, as the sensing of pipetting operations automatically identifies the well locations.

Figure 2:
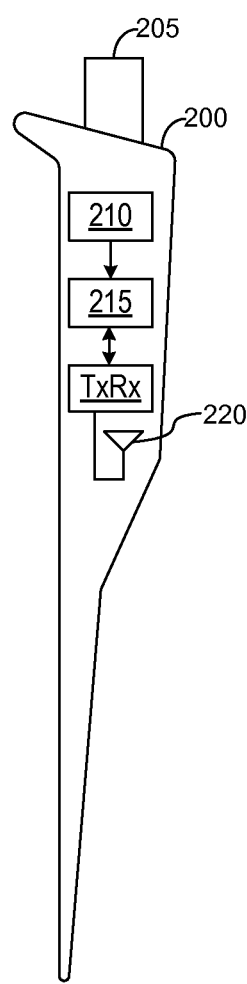
FIG. 2 depicts an embodiment of pipette 105, which includes a pipette body 200 and a thumb-activated plunger 205.

FIG. 2 depicts an embodiment of pipette 105, which includes a pipette body 200 and a thumb-activated plunger 205. Pipette 105 additionally includes a sensor 210 that communicates with plunger 205 to sense a pipetting operation and control logic 215 (e.g., a microcontroller) that receive input from sensor 210. Pipette 105 additionally includes a transmitter/receiver TxRx and an antenna 220 to facilitate communication between pipette 105 and control logic 130 (FIG. 1B). Pipette 105 can thus communicate pipette signals to controller 130 to indicate e.g. completion of a pipetting operation, an amount of reagent, or an error signal (e.g., that a plunger operation failed to take on or release a desired reagent volume). Pipette 105 can also receive information from controller 130; in one embodiment, for example, controller 130 issues user feedback to pipette 105 to indicate completion or errors in pipetting operations. Pipette can alert the user in such instances using e.g. light, sound, or vibration. In still other embodiments controller 130 may prohibit or initiate delivery or extraction of reagents from well locations based on the sensed proximity of pipette 105.

System 100 detects the tip of pipette 105 in the foregoing examples, but may similarly detect the reagent. In embodiments in which a stream of reagent is detected, sensor 125 can be used to time the stream to obtain a measure of volume. Moreover, solid reagents, such as pills, can be counted for each well location.

While the present invention has been described in connection with specific embodiments, variations of these embodiments are also envisioned. For example, when a multi-channel pipette is used, system 100 can detect and illuminate multiple locations or an area of locations. The system 100 can also detect multiple well plates with different styles e.g. 96-well or 384-well for plate-to-plate reagent transfer. These examples are in no way exhaustive, as many alternatives within the scope of the claims will be obvious to those of ordinary skill in the art. Therefore, the spirit and scope of the appended claims should not be limited to the foregoing description. Only those claims specifically reciting "means for" or "step for" should be construed in the manner required under the sixth paragraph of 35 U.S.C. Section 112.

What is claimed is:

1. A system for tracking a pipette with respect to a well plate, the well plate including an array of well locations defining an X axis and a Y axis, the system comprising:
   a well designator defining a well area, the well designator to selectively identify each well location responsive to control signals;
   a sensor to detect positions of the pipette with respect to the well locations in the well area;
   control logic coupled to the sensor and the well designator, the control logic to develop the control signals responsive to the detected positions, and to resolve an incidence angle of the pipette with respect to the X and Y axis responsive to the detected positions, to locate a tip of the pipette with respect to the well locations; and
   a touchscreen having a user-interface area adjacent the well area to support an interface for a user of the pipette.

2. The system of claim 1, wherein the sensor indicates one of the detected positions with reference to at least one of the X axis and the Y axis.

3. The system of claim 1, wherein the sensor indicates one of the detected positions with reference to a Z axis normal to the X and Y axes.

4. The system of claim 1, wherein the control logic illuminates the well locations based on the detected positions.

5. The system of claim 4, wherein the control logic illuminates a next well location based on prior ones of the detected positions.

6. The system of claim 1, wherein the sensor comprises arrays of photodiodes and photoreceptors.

7. The system of claim 6, wherein the photodiodes transmit light, to the photodiodes, in a plane parallel to the X and Y axes.

8. The system of claim 7, wherein the plane is one of a plurality of planes parallel to the X and Y axes and spaced along a Z axis perpendicular to the X and Y axes.

9. The system of claim 1, wherein the touchscreen encompasses the well area and the user-interface area.

10. The system of claim 9, wherein the control logic is configured to ignore touch signals from the well area.

11. The system of claim 1, wherein the sensor is separated from the well area by an adjustable separation along a Z axis perpendicular to the X axis and the Y axis.

12. The system of claim 1, further comprising a spacer for selectively controlling a spacing of the well locations from the sensor or well designator.

13. The system of claim 1, wherein the well plate comprises a rack for receiving vials at the locations.

14. The system of claim 1, wherein the well designator comprises indices for aligning the well plate relative to the well designator.

15. The system of claim 1, further comprising the pipette, wherein the pipette issues pipette signals to the control logic.

16. The system of claim 15, wherein the pipette signals indicate transfer of a reagent to or from the pipette.

17. The system of claim 16, wherein the control logic correlates the pipette signals to respective well locations.

18. The system of claim 17, wherein the control logic signals the well designator to illuminate well locations responsive to the pipette signals.

19. A method for tracking a pipette with respect to a well plate, the well plate including an array of well locations defining an X axis and a Y axis, the method comprising:
- receiving user commands via a touchscreen;
- responsive to the user commands, identifying each well location;
- receiving signals from an array of photoreceptors;
- detecting a position of the pipette, with respect to the well locations, responsive to the signals from the array of photoreceptors; and
- resolving an incidence angle of the pipette with respect to the X and Y axes responsive to the detected positions, to locate a tip of the pipette with respect to the well locations.

20. The method of claim 19, further comprising selectively illuminating ones of the well locations based on the detected position.

21. The method of claim 20, wherein selectively illuminating ones of the well locations comprising illuminating subsets of the well locations with different colors.

22. The method of claim 19, wherein the array of photoreceptors is one of a plurality of arrays of photoreceptors spaced along a Z axis perpendicular to the X and Y axes.

23. The method of claim 19, further comprising selecting a next one of the well locations responsive to the detected position.

24. A system for tracking a pipette with respect to a well plate, the well plate including an array of well locations defining an X axis and a Y axis, the system comprising:
- a well designator defining a well area, the well designator to selectively identify each well location responsive to control signals;
- a light source directing light across the well area and parallel to the X and Y axes;
- first arrays of photoreceptors arranged parallel to the X and Y axes to receive a first portion of the light, the first arrays of photoreceptors to detect positions of the pipette with respect to the well locations in the well area;
- second arrays of photoreceptors arranged parallel to the X and Y axes and spaced from the first arrays along a Z axis perpendicular to the X and Y axes, the second arrays of photoreceptors to receive a second portion of the light, the second arrays of photoreceptors to detect positions of the pipette with respect to the well locations in the well area; and
- control logic coupled to the first and second arrays and the well designator, the control logic to develop the control signals responsive to the detected positions, and to resolve an incidence angle of the pipette with respect to the X and Y axis responsive to the detected positions, to precisely locate a tip of the pipette with respect to the well locations.

25. The system of claim 24, wherein the light source comprises an array of photodiodes.

26. The system of claim 25, wherein the light sources includes arrays of photodiodes spaced along the Z axis.

27. The system of claim 24, further comprising a touchscreen coupled to the control logic to provide user input, wherein the control logic develops the control signal responsive to the detected positions and the user input.

28. The system of claim 27, wherein the touchscreen encompasses the well area and a user-interface area.

29. The system of claim 28, wherein the control logic is configured to ignore touch signals from the well area.

* * * * *